US008920335B2

(12) United States Patent
Huculak (10) Patent No.: US 8,920,335 B2
(45) Date of Patent: Dec. 30, 2014

(54) METHODS AND SYSTEMS FOR POSTERIOR SEGMENT VOLUME MEASUREMENT

(75) Inventor: John Christopher Huculak, Mission Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 528 days.

(21) Appl. No.: 13/222,655

(22) Filed: Aug. 31, 2011

(65) Prior Publication Data

US 2012/0053486 A1     Mar. 1, 2012

Related U.S. Application Data

(60) Provisional application No. 61/379,166, filed on Sep. 1, 2010.

(51) Int. Cl.
    *A61B 3/00*          (2006.01)
    *A61B 3/10*          (2006.01)
    *A61F 9/007*        (2006.01)

(52) U.S. Cl.
    CPC ............... *A61B 3/0025* (2013.01); *A61B 3/10* (2013.01); *A61F 9/00736* (2013.01)
    USPC ........... 600/558; 600/398; 600/399; 600/587; 351/205; 351/246

(58) Field of Classification Search
    CPC ............ A61B 3/10; A61B 3/117; A61B 5/00; A61B 8/10; G01N 21/49; A61M 31/00; A61M 37/00; A61M 2210/0612
    USPC ........... 600/398, 399, 587, 558; 351/205, 246
    See application file for complete search history.

(56) References Cited

U.S. PATENT DOCUMENTS

| | | | | |
|---|---|---|---|---|
| 4,141,346 A | * | 2/1979 | Dean, Jr. et al. | 600/485 |
| 4,395,258 A | | 7/1983 | Wang et al. | |
| 4,490,351 A | * | 12/1984 | Clark, Jr. | 424/9.4 |
| 5,220,360 A | * | 6/1993 | Verdooner et al. | 351/212 |
| 5,328,701 A | * | 7/1994 | Richmond et al. | 424/680 |
| 5,336,175 A | * | 8/1994 | Mames | 604/521 |
| 5,366,474 A | * | 11/1994 | Blumenkanz et al. | 606/202 |
| 5,755,684 A | * | 5/1998 | Chen | 604/35 |
| 5,860,949 A | * | 1/1999 | Chen | 604/35 |
| 6,179,829 B1 | | 1/2001 | Bisch et al. | |
| 6,290,690 B1 | * | 9/2001 | Huculak et al. | 604/521 |
| 6,837,855 B1 | * | 1/2005 | Puech | 600/452 |

(Continued)

OTHER PUBLICATIONS

International Search Report and Written Opinion issued for PCT/US2011/05055 dated Dec. 23, 2011, 9 pgs.

*Primary Examiner* — Sean Dougherty
(74) *Attorney, Agent, or Firm* — Haynes and Boone, LLP (57) ABSTRACT

Systems and methods for determining a volume of the posterior segment of an eye during a fluid-to-gas exchange are described. The determined volume of the posterior segment may be used to determine the volume of pure tamponade gas to be introduced into the posterior segment resulting in a desired tamponade gas to other gas (e.g., air) ratio, such as during an ophthalmic surgical procedure. Particularly, the systems and methods may provide for improved gas utilization, less waste, and reduced surgery time, for example, by accurately measuring the volume of the posterior segment of the eye and only using the amount of pure gas required to produce the desired ratio. Further, in some implementations, mixing of a tamponade gas is accomplished intrinsically within the posterior segment of the eye, thereby avoiding manual mixing and reducing surgery time.

21 Claims, 3 Drawing Sheets

(56) References Cited

U.S. PATENT DOCUMENTS

| | | | |
|---|---|---|---|
| 7,316,676 B2* | 1/2008 | Peyman et al. | 604/521 |
| 7,659,260 B2* | 2/2010 | Kadrmas | 514/62 |
| 7,959,570 B2* | 6/2011 | Enikov et al. | 600/398 |
| 8,230,866 B2* | 7/2012 | Hauger et al. | 128/898 |
| 8,399,006 B2* | 3/2013 | de Juan et al. | 424/422 |
| 8,496,631 B2* | 7/2013 | Brown | 604/264 |
| 2004/0039253 A1* | 2/2004 | Peyman et al. | 600/201 |
| 2005/0124894 A1* | 6/2005 | Puech | 600/450 |
| 2005/0216080 A1* | 9/2005 | Snyder | 623/6.47 |
| 2007/0078308 A1* | 4/2007 | Daly | 600/310 |
| 2007/0083150 A1* | 4/2007 | Nazarifar et al. | 604/31 |
| 2008/0027304 A1* | 1/2008 | Pardo et al. | 600/399 |
| 2008/0114372 A1* | 5/2008 | Edwards et al. | 606/107 |
| 2009/0030300 A1* | 1/2009 | Ghaboussi et al. | 600/405 |
| 2009/0157062 A1* | 6/2009 | Hauger et al. | 606/5 |
| 2011/0015512 A1* | 1/2011 | Pan et al. | 600/399 |
| 2011/0054291 A1* | 3/2011 | Enikov et al. | 600/405 |
| 2012/0069298 A1* | 3/2012 | Ng | 351/206 |

\* cited by examiner

METHODS AND SYSTEMS FOR POSTERIOR SEGMENT VOLUME MEASUREMENT

CROSS-REFERENCE TO RELATED APPLICATIONS

This application claims the benefit of U.S. Provisional Application No. 61/379,166, filed Sep. 1, 2010.

TECHNICAL FIELD

The present disclosure relates to determination of a volume of the posterior segment of the eye as well as improves the surgical procedure and gas usage efficiencies during fluid-air exchange ("FAX") and air-gas exchange of Vitreoretinal surgical procedures.

BACKGROUND

A fluid-air exchange procedure involves the infusion of air into the eye as fluid is aspirated out of the eye. An air-gas exchange, to follow, injects a volume of gas mixed with air into the eye displacing and replacing the air originally in the eye. Obtaining a desired mixture of gas and air along with ensuring that the resulting mixture delivered to the posterior segment of the eye is correct leads to excessive waste of gas and surgical time. Consequently, large volumes of these gases beyond what are needed to occupy the posterior segment are released into the environment and surgery is delayed during the gas and air mixing process.

SUMMARY

According to one aspect, the disclosure describes a system for determining a volume of the posterior segment of the eye. The system may include a collection chamber fluidically coupled to the posterior segment of the eye. The collection chamber may be adapted to receive a fluid from the posterior segment of the eye. The system may also include a gas source adapted to provide a supply of gas to the posterior segment of the eye and a controller. The controller may be adapted to receive a first input to initiate a supply of gas from gas source for introduction into the posterior segment of the eye, receive a second input to halt the supply of gas from gas source, detect a change in fluid level of the collection chamber in response to fluid evacuated from the posterior segment, and determine a volume of the posterior segment of the eye using the detected change in fluid level.

Another aspect encompasses a computer program product for determining a volume of the posterior segment of an eye. The computer program product may include machine-readable instruction operable when executed to receive a signal to evacuate fluid disposed in the posterior segment of the eye. The computer program product may also include machine-readable instructions operable when executed to receive a signal indicating an initial fluid level in the collection chamber from a level sensor adapted to monitor a fluid level in a collection chamber, and initiate a flow of gas from a gas supply, and receive a signal to stop the flow of gas. The gas supply may be fluidically coupled to the posterior segment of the eye. The signal to stop the flow of gas may indicate that fluid disposed in the posterior segment has been substantially drained from the posterior segment of the eye. Further, the machine-readable instructions may also include machine-readable instructions operable when executed to stop the flow of gas from the gas supply, receive a signal from the level sensor indicating a final fluid level in the collection chamber, and determine a volume of the posterior segment of the eye using the initial fluid level of the collection chamber and the final fluid level of the collection chamber.

A further aspect relates to a method for determining a volume of the posterior segment of an eye. The method may include determining an initial fluid level in a collection chamber in fluid communication with the posterior segment of the eye and providing a supply of gas from a gas source to the posterior segment of the eye. The gas source may be in fluid communication with the posterior segment of the eye. A volume of the posterior segment of the eye may contain a fluid. The method may also include evacuating the fluid from the posterior segment of the eye into the collection chamber with the supply of gas, determining a final fluid level in the collection chamber, and determining the volume of the posterior segment of the eye based upon a difference in the final fluid level in the collection chamber and the initial fluid level in the collection chamber.

The various aspects may include one or more of the following features. A fluid source may be adapted to provide a supply of fluid to the posterior segment of the eye, and a flow control device may be fluidically coupled to the fluid source and the gas source. The flow control device may be adapted to selectively fluidically couple the fluid source or the gas source to the posterior segment of the eye. A controller may be adapted to receive a third input to cause the flow control device to fluidically couple the fluid source to the posterior segment, receive a fourth input to initiate a flow of fluid from the fluid source to the posterior segment of the eye, receive a fifth input to halt the flow of fluid from the fluid source to the posterior segment of the eye, and receive a sixth input to fluidically couple the gas source to the posterior segment of the eye.

A controller adapted to detect a change in fluid level of the collection chamber in response to fluid evacuated from the posterior segment comprises a controller adapted to detect an initial fluid level in the collection chamber when the first input is received, and detect a final fluid level in the collection chamber when the second input is received. A level sensor may be adapted to detect a fluid level in the collection chamber. The level sensor may sense the initial fluid level of the collection chamber and the final fluid level of the collection chamber. An input device may be used to send the input to a controller for at least one of initiating supply of gas or stopping supply of gas. The input device may be a foot-operated device. A collection chamber may include a first collection chamber and a second collection chamber fluidically coupled to the first collection chamber. A controller may be adapted to detect a level of first collection chamber and transfer a volume of fluid from the first collection chamber to the second collection chamber when the detected level in the first collection chamber exceeds a selected level.

A first passageway may be fluidically coupled with the gas source and posterior segment of the eye. A second passageway fluidically coupling the posterior segment of the eye and the collection chamber. A controller may be adapted to receive an initial fluid level of the collection chamber when the first input is received, receive a final fluid level of the collection chamber when the second input is received, determine a volume change in the collection chamber based on the final fluid level and the initial fluid level, and subtract from the volume change in the collection chamber a first volume defined by the first passageway and a second volume defined by the second passage way. A controller may be is adapted to cause a display to display the determined volume of the posterior segment of the eye. A source of tamponade gas may be adapted to be selectively fluidically couple to the posterior segment of the eye and supply an amount of tamponade gas thereto. A controller may be adapted to determine an amount of tamponade gas to introduce to the posterior segment of the eye based on the determined volume of posterior segment of the eye and a desired concentration of the tamponade gas.

The various aspects may also include one or more of the following features. A level sensor may be adapted to detect a selected level in the collection chamber has been exceeded. A pump may transfer a portion of the fluid in the collection chamber to a supplemental container in response to the detected fluid level in excess of the selected level. The level sensor may detect that the fluid level in the collection chamber has lowered below the selected level. The pump may halt pumping of fluid from the collection chamber to the supplemental chamber.

The volume of a posterior segment of an eye may be determined by determining a volume change in the collection chamber based on the final fluid level and the initial fluid level, determining a total volume transferred by combining a volume transferred to the supplemental container with the volume change in the collection chamber, and subtracting from the total volume transferred a first volume defined by the first passageway and a second volume defined by the second passage way. A flow of gas may be initiated to evacuate substantially all of the fluid from a first passageway fluidically coupling the gas supply and the posterior segment of the eye, the posterior segment of the eye, and a second passageway fluidically coupling the posterior segment of the eye and the collection chamber. A volume of the posterior segment of the eye may be determined by determining a volume change in the collection chamber based on the final fluid level and the initial fluid level and subtracting from the volume change in the collection chamber a first volume defined by the first passageway and a second volume defined by the second passage way.

The various aspects may further include one or more of the following features. Determining an initial level in a collection chamber in fluid communication with the posterior segment of the eye may include signaling to a controller to receive a fluid level signal from a fluid level sensor adapted to measure a fluid level in the collection chamber, the controller and the fluid level sensor communicably coupled. Signaling to a controller to receive a fluid level signal from a fluid level sensor adapted to measure a fluid level in the collection chamber by manipulating an input device communicable coupled to the controller. Determining a final fluid level in the collection chamber may include signaling to a controller to receive a fluid level signal from a fluid level sensor adapted to measure a fluid level in the collection chamber. The controller and the fluid level sensor may be communicably coupled.

Evacuating the fluid from the volume of the posterior segment of the eye into the collection chamber with the supply of gas may include evacuating fluid disposed a first passageway fluidically coupling the gas supply to the posterior segment of the eye, evacuating fluid disposed in the volume of the posterior segment of the eye, and evacuating fluid disposed in a second passageway coupling the posterior segment of the eye with the collection chamber. Determining an initial level in a collection chamber in fluid communication with the posterior segment of the eye may include signaling to a controller to receive a fluid level signal from a fluid level sensor adapted to measure a fluid level in the collection chamber. The controller and the fluid level sensor may be communicably coupled. Determining a final fluid level in the collection chamber may include signaling to a controller to receive a fluid level signal from the fluid level sensor. Determining the volume of the posterior segment of the eye based upon a difference in the final fluid level in the collection chamber and the initial fluid level in the collection chamber may include determining, with the controller, a collection chamber volume change, the collection chamber volume comprising a difference of the final fluid level of the collection chamber and the initial fluid level of the collection chamber; and determining, with the controller, the volume of the posterior segment of the eye by subtracting from the collection chamber volume change the volume of the first passageway and the volume of the second passageway.

DETAILED DISCLOSURE

The present disclose describes improved systems and methods for determining a volume of the posterior segment of an eye. The determined volume may be used to introduce a tamponade gas mixture to the posterior segment in a more efficient manner thereby eliminating excessive waste of tamponade gas and surgical time. Therefore, the improved system and methods provide for improved gas utilization and less waste, for example, by accurately measuring a volume of the posterior segment of the eye. Further, in some implementations, mixing of a tamponade gas is accomplished intrinsically within the posterior segment of the eye, thereby avoiding manual mixing. The tamponade gas may be delivered to the eye during ophthalmic surgical procedures, such as a vitreoretinal surgical procedure.

Figure 1:
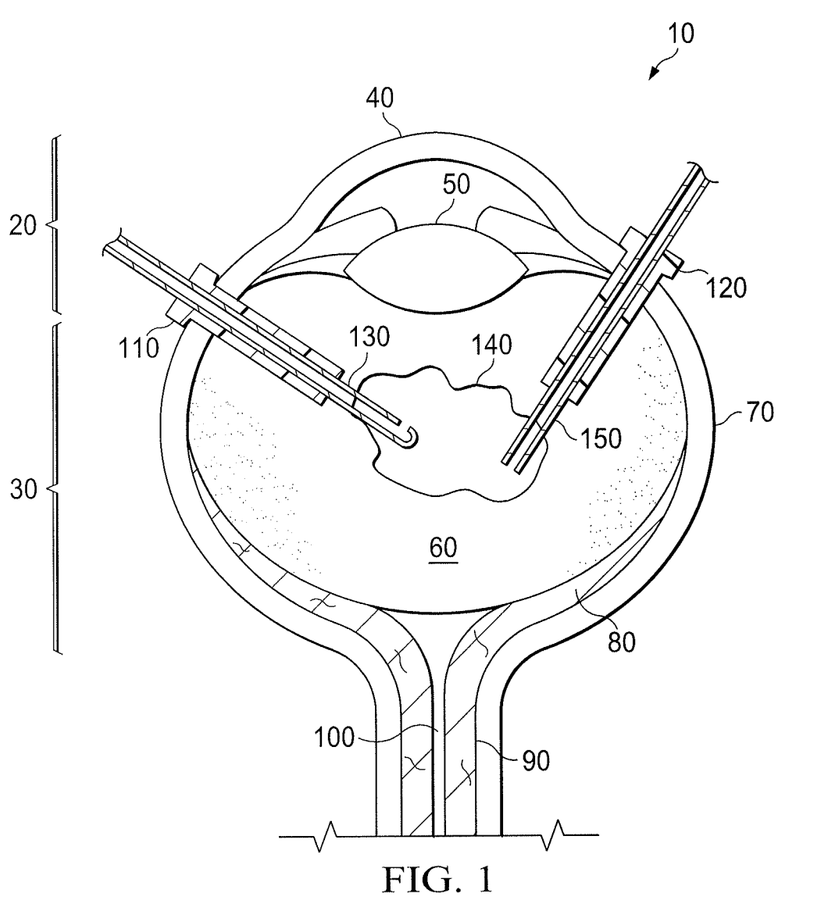
FIG. 1 is cross sectional view of an eye undergoing a vitreoretinal surgical procedure.

FIG. 1 shows a cross-sectional view of eye 10. The eye 10 includes an anterior segment 20 and a posterior segment 30. The cornea 40 and lens 50 are found within the anterior segment 20. Vitreous humor (also referred to as "vitreous") 60, a jelly-like substance, occupies the volume defined by the posterior segment 30. Also shown are the sclera 70, retina 80, optic nerve 90, and retinal artery 100.

During some ophthalmic surgical procedures, such as vitreoretinal surgical procedures involving retina reattachment, vitreous humor is removed from the posterior segment of the eye 10. Removal of the vitreous 60 is a procedure referred to as a vitrectomy. During a three port vitrectomy, cannulae, such as cannulae 110 and 120, may be inserted into the posterior segment 30 through the sclera 70, for example, in the area of the pars plana. An endoilluminator may be inserted into a third cannula, for example, a cannula that may be similar to cannulae 110, 120. The cannula for insertion of the endoilluminator may be introduced into the eye at a location similar to that of cannula 110 or cannula 120 at a location, for example, outside of the plane represented in FIG. 1. The endoilluminator may be used to provide illumination within the eye. This illumination may be used by the surgeon during the procedure. Other instruments may also be inserted into the eye through one or more of the cannulae during the procedure During a vitrectomy, the vitreous humor 60 may be removed with a cutting instrument, such as a vitcutter 130. The vitcutter 130 may be inserted into the eye through a cannula, such as cannula 110. The vitcutter 130 may be operable to both cut the vitreous 60 and aspirate the cut vitreous. As the vitreous 60 is cut and removed, a void 140 is created in the eye 10. To keep the eye from collapsing, fluid is infused into the eye 10. An infusion cannula 150 may be introduced into the eye 10, such as through cannula 120, and infusion fluid conveyed therethrough to maintain intraocular pressure. Cutting may be continued until the vitreous 60 is substantially removed from the eye 10.

The vitreous 60 may be removed to relieve traction and/or provide access to the retina 80, such as to repair damage, reattach the retina, or perform some other procedure or treatment. For the purposes of discussion, retinal reattachment is described. However, this discussion is provided merely as an example and is not intended to limit the scope of disclosure. Thus, any intraocular procedure that may include introduction of a gas into the eye and/or measurement of a volume of the posterior segment of the eye is intended to be encompassed by this disclosure.

In some implementations, vitreoretinal surgical procedures may be performed on a vitreoretinal surgical console, such as the Constellation® Vision System produced by Alcon Laboratories, Inc. of 6201 South Freeway, Fort Worth, Tex. 76134. Other surgical devices and/or consoles may be used without departing from the scope of the disclosure.

At or near the conclusion of a retinal reattachment/repositioning procedure when the retina 80 has be placed in a desired location, the infusion fluid may be exchanged for air (a process referred to as fluid/air exchange, interchangeably referred to as "FAX"). A long acting tamponade gas, mixed with air, may then be introduced into the eye 10 (a process referred to as air/gas exchange). Example tamponade gases include $C_3F_8$, $SF_6$, and $C_2F_6$, although others may also be used. The tamponade gas/air mixture (hereinafter referred to as "tamponade gas mixture") may be introduced to keep the retina 80 in position. To eliminate or significantly reduce waste of these gases, the posterior segment 30 into which the gas is to be injected may be measured and only a small portion of 100% gas injected into the posterior segment.

Figure 2:
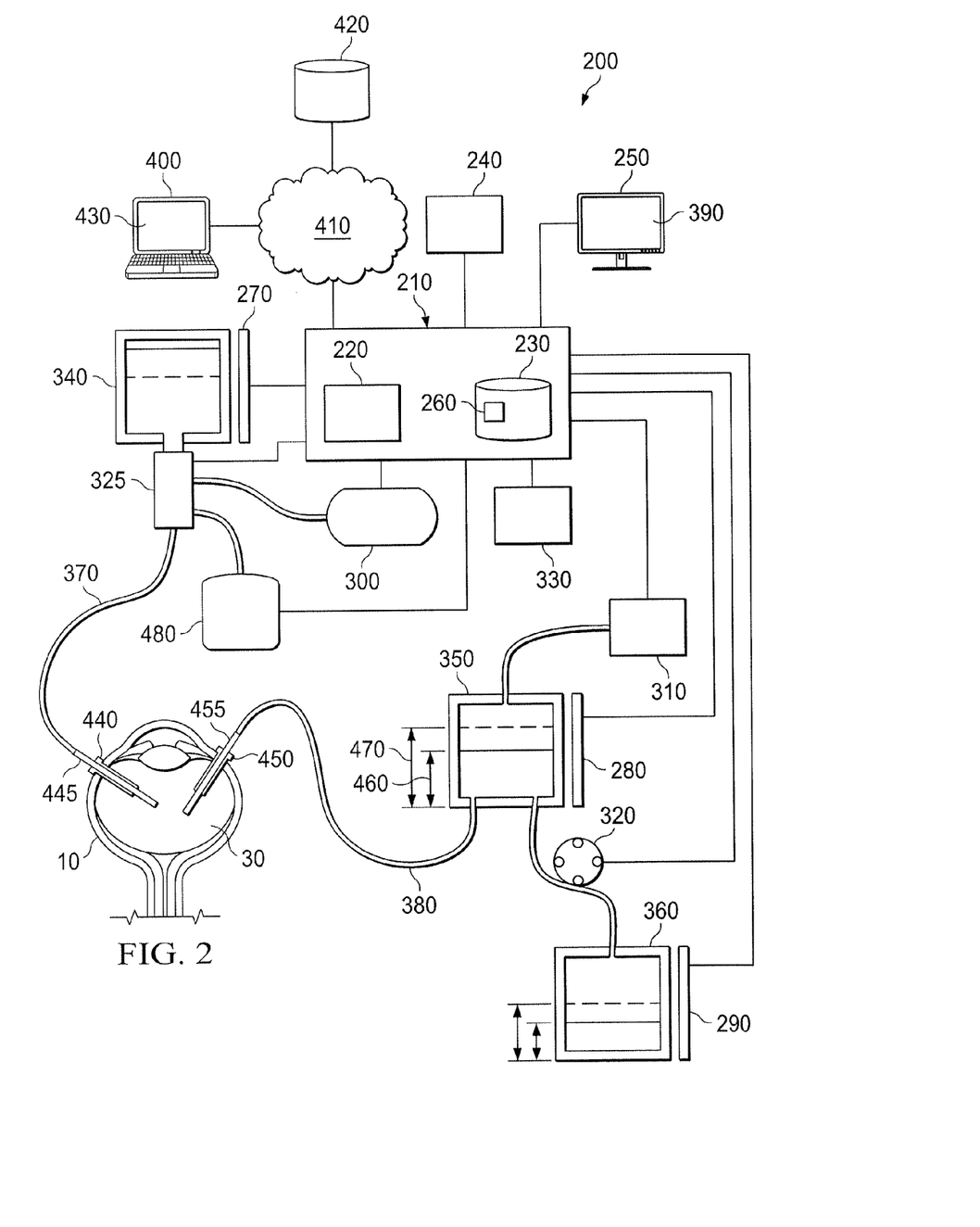
FIG. 2 is an example system for use in a vitreoretinal surgical procedure.

FIG. 2 shows an example system 200 for performing a FAX procedure with measurement of the volume of aspirated fluid. The system 200 may include a controller 210 including a processor 220, memory 230, one or more input devices 240, and one or more output devices, such as a display 250. The one or more input devices 240 may include a keypad, touch screen, mouse, a foot-operated input device, or any other desired input device. The system 200 may also include other features, such as those described in more detail below. Further, the system 200 may be a stand-alone system. Alternately, system 200 may be incorporated into a surgical console, such as the Constellation Vision System, described above, or other surgical console or system.

The system 200 may also include level sensors 270, 280, 290, gas supply 300, vacuum device 310, a pump 320, such as peristaltic pump, a flow control valve 325 as well as one or more other sensors or components, generically referred to as 330. In some implementations, the gas supply 300 may contain a volume of air or other gas or gas mixture. Level sensors 270, 280, and 290 may be operable to detect a fluid level in an infusion fluid source 340, collection chamber 350, and container 360, respectively. In some implementations, container 360 may be a drain bag. In some implementations, a fluid level in the container 360 may be determined in an alternate manner. For example, the fluid volume in container 360 may be determined by utilizing a pump rate from the pump 320, correlating the pump rate to a flow rate, and integrating the flow rate over time to determine a volume. Such a feature may be used in addition to or in replacement of the level sensor 290.

Infusion tubing 370 may extend between the infusion fluid source 340 and the eye 10. Aspiration tubing 380 may extend between the eye 10 and the collection chamber 350. Internal passages formed within the infusion tubing 370 and aspiration tubing 380 provide a conduit for conducting fluids into and out of the eye 10. In some instances, the infusion tubing 370 and the aspiration tubing 380 may be of a known or standard size or gauge. As such, a cross sectional area of the internal passageway of the infusion tubing 370 and aspiration tubing 380 may be known. For example, the internal passageways may have a circular cross-section, and a diameter of the internal passageways may be known. The volume may be determined by multiplying a length of the infusion tubing 320 or aspiration tubing 330 by the area of the internal passageway. Accordingly, the volume defined by a passageway passing through the infusion tubing 320 and aspiration tubing 330 may be known or determined. However, the internal passageways may have any desired cross-section and the volume of the internal passageways may be otherwise known.

The controller 210 may be operable to receive, transmit, process, and store data associated with system 200. Generally, FIG. 2 provides merely one example of controllers within the scope of the disclosure. Each controller is generally intended to encompass any suitable processing device. For example, although FIG. 2 illustrates an example controller 210 that may be used with the disclosure, system 200 can be implemented using other types of controllers. Indeed, controller 210 may be any computer or processing device such as, for example, a blade server, general-purpose personal computer (PC), Macintosh, workstation, Unix-based computer, or any other suitable device. In other words, the present disclosure contemplates computers other than general purpose computers as well as computers without conventional operating systems. Controller 210 may be adapted to execute any operating system including Linux, UNIX, Windows Server, or any other suitable operating system. According to one embodiment, controller 210 may also include or be communicably coupled with a web server and/or a mail server.

Memory 230 may include any memory or database module and may take the form of volatile or non-volatile memory including, without limitation, magnetic media, optical media, random access memory (RAM), read-only memory (ROM), removable media, or any other suitable local or remote memory component. Illustrated memory 230 may include, among other items, a posterior segment volume determination application 260. The application 260 may provide instructions for operating aspects of the surgical system, such the system 200, in determining posterior segment volume of an eye.

Memory 230 may store classes, frameworks, applications, backup data, jobs, or other information that includes any parameters, variables, algorithms, instructions, rules, or references thereto. Memory 230 may also include other types of data, such as environment and/or application description data, application data for one or more applications, as well as data involving virtual private network (VPN) applications or services, firewall policies, a security or access log, print or other reporting files, HyperText Markup Language (HTML) files or templates, related or unrelated software applications or subsystems, and others. Consequently, memory 230 may also be considered a repository of data, such as a local data repository from one or more applications. Memory 230 may also include data that can be utilized by the application 260.

Application 260 may include a program or group of programs containing instructions operable to utilize received data, such as in one or more algorithms, to determine a result or output. The determined results may be used to affect an aspect of the system 200. The application 260 may include instructions for determining a volume of a posterior segment of an eye and for controlling one or more aspects of the system 200 in furtherance thereof. For example, the application 260 may determine one or more adjustments to the system 200. The adjustments may be implemented by one or more transmitted control signals to one or more components of system 200. While an example system 200 is shown, other implementations of the system 200 may include more, fewer, or different components than those shown.

Processor 220 executes instructions and manipulates data to perform the operations of the system 200, e.g., computational and logic operations, and may be, for example, a central processing unit (CPU), a blade, an application specific integrated circuit (ASIC), or a field-programmable gate array (FPGA). Although FIG. 2 illustrates a single processor 220, multiple processors may be used according to particular needs and reference to processor 220 is meant to include multiple processors where applicable. For example, the processor 220 may be adapted for receiving information from data from various components of the system 200, process the received data, and transmit data to one or more of the components of the system 200 in response thereto. For example, the processor 220 may send and/or receive data to and/or from level sensors 270, 280, 290, gas supply 300, vacuum device 310, pump 320, the one or more other sensors or components 330, as well as other components that may be included in the system 200. The processor 220 may execute application 260 to perform posterior segment volume determination activities and send and receive data to portions of the system 200 to effectuate those activities.

Further, the processor 220 may transmit control signals to one or more of the components. For example, the processor 220 of system 200 may transmit control signals in response to received data. In some implementations, the processor 220 may execute the application 260 and transmit control signals to system components in response thereto. In the example system 200 shown in FIG. 1, for example, the processor 220 may transmit control signals to one or more valves, such as valve 325, the gas supply 300, the vacuum device 310, the pump 320, or other component of the system 200.

The display 250 displays information to a user, such as a medical practitioner. In some instances, the display 250 may be a monitor for visually displaying information. In some instances, the display 250 may operate both as a display and an input device. For example, the display 250 may be a touch sensitive display in which a touch by a user or other contact with the display produces an input to the system 200. The display 250 may present information to the user via a graphical user interface or application interface (collectively referred to as "GUI 390").

GUI 390 may include a graphical user interface operable to allow the user, such as a medical practitioner, to interface with the system 200 for any suitable purpose, such as viewing application or other system information. For example, GUI 390 could provide information associated with a medical procedure, including detailed information related to a vitreoretinal surgical procedure. For example, the GUI 390 could provide infusion or aspiration pressure or flow rate information, fluid level information, posterior segment volume information, or any other desired information associated with an operation or condition of system 200 or information associate with application 260.

Generally, GUI 390 may provide a particular user with an efficient and user-friendly presentation of information received by, provided by, or communicated within system 200. GUI 390 may include a plurality of customizable frames or views having interactive fields, pull-down lists, and buttons operated by the user. GUI 390 may also present a plurality of portals or dashboards. For example, GUI 390 may display a secure webpage that allows users to input and define parameters associated with the vitreoretinal surgical procedures. It should be understood that the term graphical user interface may be used in the singular or in the plural to describe one or more graphical user interfaces and each of the displays of a particular graphical user interface. Indeed, reference to GUI 390 may indicate a reference to the front-end or a component of application 260 without departing from the scope of this disclosure. Therefore, GUI 390 contemplates any graphical user interface. For example, in some instances, the GUI 390 may include a generic web browser or touch screen that processes information in system 200 and efficiently presents the results to the user. In other instances, the GUI 390 may include a custom or customizable interface for displaying and/or interacting with the various features of the application 260 or other system services.

In some implementations, the system 200 may be in communication with one or more local or remote computers, such as computer 400, over a network 410. Network 410 facilitates wireless or wireline communication between controller 210 and, generally, system 200 and any other local or remote computer, such as computer 400. For example, medical practitioners may use the computer 400 to interact with activities associated with operation of the system 200, including the services provided by the application 260. Network 410 may be all or a portion of an enterprise or secured network. In another example, network 410 may be a VPN merely between controller 210 and computer 400 across wireline or wireless link. Such an example wireless link may be via 802.11a, 802.11b, 802.11g, 802.20, WiMax, ZigBee, Ultra-Wideband and many others. While illustrated as a single or continuous network, network 410 may be logically divided into various sub-nets or virtual networks without departing from the scope of this disclosure, so long as at least a portion of network 410 may facilitate communications among controller 210, computer 400, and other devices.

For example, controller 210 may be communicably coupled to a repository 420 through one sub-net while communicably coupled to computer 400 through another. In other words, network 410 encompasses any internal or external network, networks, sub-network, or combination thereof operable to facilitate communications between various computing components in system 200. Network 410 may communicate, for example, Internet Protocol (IP) packets, Frame Relay frames, Asynchronous Transfer Mode (ATM) cells, voice, video, data, and other suitable information between network addresses (collectively or interchangeably referred to as "information"). Network 410 may include one or more local area networks (LANs), radio access networks (RANs), metropolitan area networks (MANs), wide area networks (WANs), all or a portion of the global computer network known as the Internet, and/or any other communication system or systems at one or more locations. In certain embodiments, network 410 may be a secure network accessible to users via certain local or remote computer 400.

Computer 400 may be any computing device operable to connect or communicate with controller 210 or network 410 using any communication link. In some instances, computer 400 may include an electronic computing device operable to receive, transmit, process, and store any appropriate data associated with system 200. Computer 400 may also include or execute a GUI 430. GUI 430 may similar to GUI 390. It will be understood that there may be any number of computers 400 communicably coupled to system 200. Moreover, for ease of illustration, each computer 400 is described in terms of being used by one user. But this disclosure contemplates that many users may use one computer or that one user may use multiple computers.

As used in this disclosure, computer 400 is intended to encompass a personal computer, touch screen terminal, workstation, network computer, kiosk, wireless data port, smart phone, personal data assistant (PDA), one or more processors within these or other devices, or any other suitable processing device. For example, computer 400 may be a PDA operable to wirelessly connect with an external or unsecured network. In another example, computer 400 may be a laptop computer that includes an input device, such as a keypad, touch screen, mouse, or other device that can accept information, and an output device that conveys information associated with the operation of system 200 or computer 400, including digital data, visual information, or user interface, such as GUI 430. Both input devices and output devices may include fixed or removable storage media such as a magnetic computer disk, CD-ROM, or other suitable media to both receive input from and provide output to users of computer 400 through, for example, a display.

FIG. 2 illustrates the example system 200 being used a vitreoretinal surgical procedure. A patient's eye 10 has both an infusion cannula 440, which may or may not be similar to infusion cannula 150, and an aspiration cannula 450 inserted into the eye 10. An infusion probe 445 may be inserted into the eye through the infusion cannula 440. An aspiration probe 455 may be inserted into the eye 10 through aspiration cannula 450. During an intraocular surgical procedure to repair or otherwise treat the retina, fluid may be aspirated from the eye via the aspiration probe 455 and infusion fluid may then be supplied to the eye 10 via the infusion probe 445. Aspiration from the eye and fluid infusion into the eye 10 may be carefully monitored to control intraocular pressure.

The infusion fluid may be supplied from an infusion fluid source 340. In some instances, the infusion fluid source 340 may be a container of infusion fluid. Pressure of the infusion fluid may be controlled in various ways. In some instances, infusion fluid pressure may be controlled by vertically adjusting a height of the infusion fluid source 340. For example, the infusion fluid source 340 may be provided on a vertically adjustable pole, such as a motorized telescoping pole. In other instances, pressure of the infusion fluid source 340 may be controlled by a pump. An example pump may be a pressurized cuff circumjacent the source 340. Aspiration fluid pressure may be controlled by controlling an aspiration flow rate, such as by adjusting a vacuum of the vacuum device 310. The controller 210 may receive infusion pressure and/or aspiration pressure data from one or more components of the system 200. For example, infusion pressure data may include pole height data or pump pressure data. Aspiration pressure data may include vacuum pressure data.

Infusion fluid may be supplied to the eye 10 during the course of a vitreoretinal surgical procedure. For vitreoretinal surgical procedures involving macular holes, retinal breaks, retinal tears, etc, such as during a retina reattachment surgery, a fluid/air exchange may be performed to allow positioning and reattachment of the retina. Fluid may be aspirated from the eye 10, allowing air to be infused into the eye 10 in replacement of the fluid volume removed. The fluid/air exchange may be completed with the aspiration of all or substantially all of the fluid in the eye 10. Infusion of air into the eye may be stopped upon aspiration of all or substantially all of the fluid in the eye 10.

A tamponade gas (e.g., $C_3F_8$, $SF_6$, and $C_2F_6$) may also be introduced into the eye to keep the retina in place for a period of time following the surgical procedure. In preparation for introducing the tamponade gas into the posterior segment, a medical practitioner may set a desired mixture ratio of the tamponade gas and air. In some cases, the mixture may be an air/tamponade gas mixture, although any suitable gas or gases may be combined with the tamponade gas for forming the tamponade gas mixture. Example mixture ratios may be 20% tamponade gas and less with the deficit composed of air. However, any desired gas/air mixture ratio may be used. Further, while the term "gas-to-air ratio" or "gas-to-air mixture ratio" may be used, it is understood that a gas or gasses other than air may be used to form the tamponade gas mixture.

A user, such as a medical practitioner, may initiate the FAX by interacting with the controller 210 via the display 250, foot-operated input device, or in some other way. In response, the controller 210 may send a signal actuate the valve 325 to stop the flow of infusion fluid and allow a gas flow from the gas supply 300 through the infusion tubing 370. In some instances, the gas provided by the gas supply 300 may be air or any other desired or suitable gas. For purposes of explanation, the gas provided from the gas supply 300 will be described hereinafter as air, appreciating that air is a mixture of different gases. However, it will be understood that any desired or suitable gas may be supplied from the gas supply 300.

Further, an initial fluid level 460 of a collection chamber 350 may be determined, such as by the level sensor 280, transmitted to the controller 210, and stored. The air may be introduced into the infusion tubing 370 via the valve 325. The vacuum device 310 may generate a vacuum urging the infusion fluid into the collection chamber 350. As the FAX progresses, the vacuum produced by the vacuum device 310 draws fluid from the posterior segment 30, which draws air from the gas supply 300 through the infusion tubing 370 and into the posterior segment 30 of the eye 10. The infusion fluid is aspirated from the eye 10 via the aspiration probe 455. Aspiration of the infusion fluid may continue until all or substantially all of the infusion fluid is removed from the aspiration tubing 370, the posterior segment 30 of the eye 10, and the aspiration tubing 380.

The infusion fluid displaced by the infused air may be collected in the collection chamber 350. Completion of the FAX may be signaled by, for example, an interaction by the user with a component of the system 200, such as the display 250, foot-operated input device, or in some other way. The controller 210 may receive the signal indicating the end of the FAX and cause the final fluid level 470 to be detected, such as by the level sensor 280, and stored. In some instances, fluid levels in the collection chamber 350 may be detected visually.

In some instances, the volume of the posterior segment 30 of the eye 10 may be determined by determining a volume of fluid aspirated during the FAX ("aspirated volume"). For example, the aspirated volume may be determined by calculating a difference between the final fluid level 470 and the initial fluid level 460 of the collection chamber 350. A volume of the posterior segment 30 may be determined by subtracting the volumes of internal passages of the infusion tubing 370 and the aspiration tubing 380 from the aspirated volume. In some instances, the volume of the posterior segment 30 may be determined manually. In other instances, the volume may be determined automatically by the controller 210. For example, the controller 210 may utilize application 260 to automatically determine the volume of the posterior segment 30 of the eye 10. The determined volume of the posterior segment 30 may be displayed on the display 250, such as in GUI 390.

In other implementations, prior to initiation of the FAX, the vacuum device 310 may be disabled and the fluid in the collection chamber 350 may be drained. The vacuum device 310 may be re-enabled and the FAX commenced. At completion of the FAX, the posterior segment 30 of the eye 10 may be determined by determining the final fluid level 470 of the collection chamber 350 and subtracting therefrom the volumes of the internal passages of the infusion tubing 370 and the aspiration tubing 380.

In another implementation, the container 360 may be utilized to accept fluid aspirated to the collection chamber 350 that causes the collection chamber 350 to exceed a selected fluid level therein. For example, as the aspirated fluid is collected in the collection chamber 350, the level sensor 280 monitors the fluid level therein. When the designated fluid level in the collection chamber 350 is exceeded, the pump 320 may begin pumping fluid from the collection chamber 350 to the container 360. In some instances, the fluid level in the container 360 may be identified or otherwise recorded at the time the FAX is initiated. For example, the fluid level in the container 360 may be identified by level sensor 290, visually, or in any other desired or suitable manner. At the conclusion of the FAX, the fluid level in the container 360 may also be identified. The fluid volume transferred to the container 360 may be determined by taking the difference between the fluid level at the beginning and conclusion of the FAX. Alternatively, the fluid volume transferred to the container 390 may be determined by utilizing a pump rate from pump 320, correlating the pump rate to a flow rate, and integrating the flow rate over time. The volume of the posterior segment 30 may be determined by calculating a difference between the final fluid level 470 and the initial fluid level 460 of the collection chamber 350, subtracting therefrom the volumes of internal passages of the infusion tubing 370 and the aspiration tubing 380, and adding the fluid volume transferred to the container 360.

In still other implementations, after air from the gas supply 300 has been introduced into the infusion tubing 370 via the valve 325, a user may indicate both a start point when gas is seen entering the posterior segment 30 and an end point when the all fluid is evacuated from the posterior segment 30 but prior to any air entering the aspiration tubing 380. The user may indicate the start and stop point via an interaction with the foot-operated device, the display, or any other desired or suitable interaction with the system 200. The fluid levels in the collection chamber 350 corresponding to the start and stop points may be determined and stored. The volume of the posterior segment 30 may be determined by subtracting the fluid level of the collection chamber 350 corresponding to the end point from the fluid level of the collection chamber 350 corresponding to the start point.

With the volume of the posterior segment 30 and a desired concentration of the tamponade gas for introduction into the posterior segment 30 known, an amount of the tamponade gas may be determined and an air-gas exchange may be performed. The/air-gas exchange may involve displacement or exchange of the gas present in the eye 10 with the tamponade gas mixture. Again, although air used for the FAX, other suitable gases may be used.

In some instances, the amount of tamponade gas to form the desired concentration in the posterior segment 30 may be automatically determined by the application 260. The tamponade gas may be initiated by a user via the display 250, input device 240 (such as a foot-operated input device), or in some other way. In some implementations, valve 325 may stop flow of the gas from gas supply 300 and permit flow of the tamponade gas from gas supply 480 communicably coupled to the controller 210. Because a volume to be filled and desired concentration of the tamponade gas is known, an accurate amount of the tamponade gas may be introduced into the eye 10. The tamponade gas mixes in the eye, resulting in the desired concentration.

In some implementations, a desired amount of tamponade gas may be introduced into the posterior segment 30 of the eye 10 via a cannula. For example, a portion of a needle of the syringe may be introduced into the posterior segment 30 via cannula 440 or cannula 450. For example, if cannula 440 is used, the infusion probe 445 may be withdrawn and the needle of the syringe may be inserted into the posterior segment 30 via the cannula 440.

With the volume of the posterior segment 30 determined and the desired tamponade gas concentration known, an amount of tamponade gas for forming the desired concentration ("determined tamponade volume") may be determined. A volume of 100 percent or substantially 100 percent tamponade gas may be drawn into the syringe. In some instances, an amount of tamponade gas equal to the determined tamponade volume may be drawn into the syringe. The needle of the syringe may be inserted into the cannula in the eye 10 and the determined tamponade volume of tamponade gas may be injected into the eye. Where the amount of tamponade gas in the syringe equals the determined tamponade volume, the entire amount of tamponade gas may be injected into the eye 10.

To maintain intraocular pressure ("IOP") within the posterior segment, an amount of air displaced by the injected tamponade gas may be allowed to escape from the eye 10, such as through a cannula inserted into the eye 10. The determined amount of tamponade gas injected into the eye mixes with the air present within the eye to result in the desired tamponade gas concentration. As a result, very little, if any, tamponade gas is wasted. This low waste amount is important because tamponade gases can be expensive.

In still other implementations, the determined volume of the posterior segment and desired tamponade gas concentration may be used to manually form the tamponade gas mixture and/or inject the tamponade gas mixture into the eye. For example, in some instances, the infusion tubing 370 may be decoupled from the infusion probe 445 and an injector, such as a syringe with the tamponade gas mixture, may be coupled with the cannula 440 and the tamponade gas mixture injected into the posterior segment of the eye 10.

In addition to accurately determining a volume of the posterior segment of the eye, the present disclosure provides for reduced waste of surgical time. That is, a mixture of tamponade gas for introduction into the eye may be quickly determined and produced, thereby avoiding delays during the surgical procedures. This may be important because, in some instances, a delay during surgery may necessitate a recordable event due to applicable laws or regulations.

Figure 3:
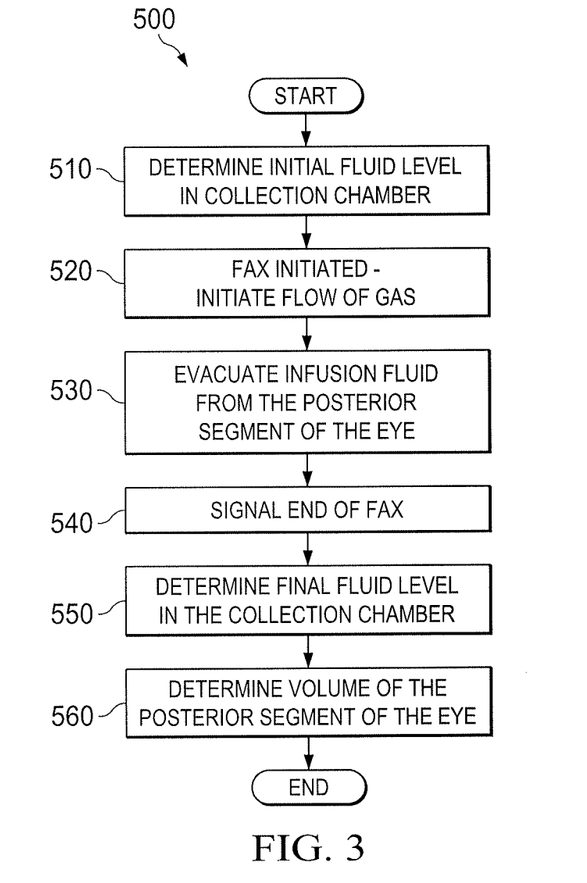
FIG. 3 is an example flow chart for determining a volume of a posterior segment of the eye.

FIG. 3 shows an example flow chart 500 for determining a volume of the posterior segment 30 of eye 10. As explained above and according to some implementations, the FAX may be triggered by an input to the controller 210. At 510, an initial fluid level 460 in the collection chamber 350 may be determined. In some instances, an initial fluid level 460 may be determined automatically by a surgical system, such as example surgical system 200. For example, the surgical system may determine the initial fluid level upon a received input from a user, such as a surgeon. For example, the level sensor 280 may sense a fluid level in the collection chamber 350 and transmit that fluid level to the controller 210. At 520, FAX is initiated, and a gas is introduced to remove infusion fluid from the eye 10. For example, gas, such as air, may be introduced into a fluid circuit. In some instances, the fluid circuit may be formed from infusion tubing, the posterior segment of the eye, and aspiration tubing. At 530, the infusion fluid is evacuated from the posterior segment of the eye. For example, the infusion fluid may be evacuated from the fluid circuit by the introduced gas. At 540, the FAX is stopped. The FAX may be stopped by an input to the controller 210, as explained above. At 550, the final fluid level 470 in the collection chamber 350 may be determined. At 560, the volume of the posterior segment 30 may be determined. For example, the volume of the posterior segment 30 may be determined by subtracting the final fluid level 470 from the initial fluid level 460 to determine the total fluid transferred. From this number the volumes of the passageways extending through the infusion tubing 370 and aspiration tubing 380 may be subtracted. In other implementations, an amount of fluid transferred to the container 360 may be determined. Consequently, the volume of the posterior segment 30 may be determined by adding the total amount of volume transferred to the collection chamber 350 and adding thereto the volume transferred to the container 360. From this amount, the volume of the passageways of the infusion tubing 370 and aspiration tubing 380 may be subtracted to determine the volume of the posterior segment 30.

It should be understood that, although many aspects have been described herein, some implementations may include all of the features, while others may include some features while omitting others. That is, various implementations may include one, some, or all of the features described herein.

A number of implementations have been described. Nevertheless, it will be understood that various modifications may be made without departing from the spirit and scope of the disclosure. Accordingly, other implementations are within the scope of the following claims.

What is claimed is:

1. A system for determining a volume of a posterior segment of an eye, the system comprising:
   a collection chamber fluidically coupled to the posterior segment of the eye, the collection chamber adapted to receive a fluid from the posterior segment of the eye;
   a gas source adapted to provide a supply of gas to the posterior segment of the eye; and
   a controller adapted to:
      receive a first input to initiate the supply of gas from the gas source for introduction into the posterior segment of the eye;
      receive a second input to halt the supply of gas from the gas source;
      detect a change in fluid level of the collection chamber in response to fluid evacuated from the posterior segment; and
      determine a volume of the posterior segment of the eye using the detected change in fluid level.

2. The system of claim 1, further comprising:
   a fluid source adapted to provide a supply of the fluid to the posterior segment of the eye; and
   a flow control device fluidically coupled to the fluid source and the gas source, the flow control device adapted to selectively fluidically couple the fluid source or the gas source to the posterior segment of the eye, and wherein the controller is further adapted to:
      receive a third input to cause the flow control device to fluidically couple the fluid source to the posterior segment;
      receive a fourth input to initiate a flow of the fluid from the fluid source to the posterior segment of the eye;
      receive a fifth input to halt the flow of the fluid from the fluid source to the posterior segment of the eye; and
      receive a sixth input to fluidically couple the gas source to the posterior segment of the eye.

3. The system of claim 1, wherein the controller is further adapted to:
   detect an initial fluid level in the collection chamber when the first input is received; and
   detect a final fluid level in the collection chamber when the second input is received.

4. The system of claim 3, further comprising a level sensor adapted to detect the fluid level in the collection chamber, the level sensor being adapted to sense the initial fluid level of the collection chamber and the final fluid level of the collection chamber.

5. The system of claim 1, further comprising an input device for sending at least one of the first and second inputs to the controller for at least one of initiating the supply of gas or stopping the supply of gas.

6. The system of claim 4, wherein the input device comprises a foot-operated device.

7. The system of claim 1, wherein the collection chamber comprises:
   a first collection chamber; and
   a second collection chamber fluidically coupled to the first collection chamber, wherein the controller is further adapted to detect a level of the first collection chamber and transfer a volume of fluid from the first collection chamber to the second collection chamber when the detected level in the first collection chamber exceeds a selected level.

8. The system of claim 1, further comprising:
   a first passageway fluidically coupling the gas source and the posterior segment of the eye; and
   a second passageway fluidically coupling the posterior segment of the eye and the collection chamber,
   wherein the controller is further adapted to:
      receive an initial fluid level of the collection chamber when the first input is received;
      receive a final fluid level of the collection chamber when the second input is received;
      determine a volume change in the collection chamber based on the final fluid level and the initial fluid level; and
      subtract from the volume change in the collection chamber a first volume defined by the first passageway and a second volume defined by the second passageway.

9. The system of claim 1, further comprising a display, wherein the controller is adapted to cause the display to display the determined volume of the posterior segment of the eye.

10. The system of claim 1, further comprising a source of tamponade gas adapted to be selectively fluidically coupled to the posterior segment of the eye and supply an amount of the tamponade gas thereto, and wherein the controller is further adapted to determine an amount of the tamponade gas to introduce to the posterior segment of the eye based on the determined volume of the posterior segment of the eye and a desired concentration of the tamponade gas.

11. A computer program product for determining a volume of a posterior segment of an eye, the computer program product comprising machine-readable instructions embodied on a non-transitory tangible media operable when executed to:
   receive a first signal to evacuate fluid disposed in the posterior segment of the eye;
   receive a second signal from a level sensor adapted to monitor a fluid level in a collection chamber, the signal indicating an initial fluid level in the collection chamber;

initiate a flow of gas from a gas supply, the gas supply fluidically coupled to the posterior segment of the eye;

receive a third signal to stop the flow of gas, the third signal indicating that fluid disposed in the posterior segment has been substantially drained therefrom;

stop the flow of gas from the gas supply based on the third signal;

receive a fourth signal from the level sensor indicating a final fluid level in the collection chamber after the flow of gas has been stopped; and determine a volume of the posterior segment of the eye using the initial fluid level of the collection chamber and the final fluid level of the collection chamber.

12. The computer program product of claim 11 further comprising machine-readable instructions operable when executed to:

detect with the level sensor that a selected level in the collection chamber has been exceeded;

initiate a pump to transfer a portion of the fluid in the collection chamber to a supplemental container in response to the detected fluid level in excess of the selected level;

detect with the level sensor that the fluid level in the collection chamber has lowered below the selected level; and stop the pump to halt pumping of fluid from the collection chamber to the supplemental chamber.

13. The computer program product of claim 12, wherein the machine-readable instructions operable when executed to determine a volume of the posterior segment of the eye using the initial fluid level of the collection chamber and the final fluid level of the collection chamber comprises machine-readable instructions operable when executed to:

determine a volume change in the collection chamber based on the final fluid level and the initial fluid level;

determine a total volume transferred by combining a volume transferred to the supplemental container with the volume change in the collection chamber; and subtract from the total volume transferred a first volume defined by the first passageway and a second volume defined by the second passageway.

14. The computer program product of claim 11, wherein the machine-readable instructions operable when executed to initiate a flow of gas from the gas supply comprises machine-readable instructions operable when executed to initiate the flow of gas to evacuate substantially all of the fluid from a first passageway fluidically coupling the gas supply and the posterior segment of the eye, the posterior segment of the eye, and a second passageway fluidically coupling the posterior segment of the eye and the collection chamber.

15. The computer program product of claim 11, wherein the machine-readable instructions operable when executed to determine a volume of the posterior segment of the eye using the initial fluid level of the collection chamber and the final fluid level of the collection chamber comprises machine-readable instructions operable when executed to:

determine a volume change in the collection chamber based on the final fluid level and the initial fluid level; and subtract from the volume change in the collection chamber a first volume defined by the first passageway and a second volume defined by the second passageway.

16. A method for determining a volume of a posterior segment of an eye with a surgical system, the method comprising:

measuring, by a fluid level sensor, an initial fluid level in a collection chamber in fluid communication with the posterior segment of the eye;

providing a supply of gas from a gas source to the posterior segment of the eye, the gas source in fluid communication with the posterior segment of the eye and a volume of the posterior segment of the eye containing a fluid;

evacuating the fluid from the volume of the posterior segment of the eye into the collection chamber with the supply of gas;

measuring, by the fluid level sensor, a final fluid level in the collection chamber; and determining, by a controller, the volume of the posterior segment of the eye based upon a difference in the final fluid level in the collection chamber and the initial fluid level in the collection chamber.

17. The method of claim 16, wherein measuring the initial fluid level comprises signaling to a controller to receive a fluid level signal from the fluid level sensor adapted to measure a fluid level in the collection chamber, the controller and the fluid level sensor being communicably coupled.

18. The method of claim 17, wherein signaling to the controller comprises manipulating an input device communicably coupled to the controller.

19. The method of claim 16, wherein determining the final fluid level in the collection chamber comprises signaling to the controller to receive a fluid level signal from the fluid level sensor adapted to measure a fluid level in the collection chamber, the controller and the fluid level sensor being communicably coupled.

20. The method of claim 19, wherein signaling to the controller comprises manipulating an input device communicably coupled to the controller.

21. The method of claim 16, wherein evacuating the fluid from the volume of the posterior segment of the eye into the collection chamber with the supply of gas comprises:

evacuating fluid disposed in a first passageway fluidically coupling the gas supply to the posterior segment of the eye;

evacuating the fluid disposed in the volume of the posterior segment of the eye; and evacuating fluid disposed in a second passageway fluidically coupling the posterior segment of the eye with the collection chamber, wherein measuring the initial fluid level in the collection chamber comprises signaling to the controller to receive a fluid level signal from the fluid level sensor adapted to measure a fluid level in the collection chamber, the controller and the fluid level sensor being communicably coupled, wherein determining the final fluid level in the collection chamber comprises signaling to the controller to receive a fluid level signal from the fluid level sensor, and wherein determining the volume of the posterior segment of the eye based upon the difference in the final fluid level in the collection chamber and the initial fluid level in the collection chamber comprises:

determining, by the controller, a collection chamber volume change, the collection chamber volume change comprising a difference of the final fluid level of the collection chamber and the initial fluid level of the collection chamber; and determining, by the controller, the volume of the posterior segment of the eye by subtracting from the collection chamber volume change the volume of the first passageway and the volume of the second passageway.

* * * * *